US00PP34753P2

(12) United States Plant Patent
Dirr

(10) Patent No.: US PP34,753 P2
(45) Date of Patent: Nov. 22, 2022

(54) ***DISTYLIUM* PLANT NAMED 'DISMD-09-15'**

(50) Latin Name: ***Distylium* sp. hybrid**
Varietal Denomination: DISmd-09-15

(71) Applicant: University of Georgia Research Foundation, Inc., Athens, GA (US)

(72) Inventor: Matthew A. Dirr, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/726,883

(22) Filed: Apr. 22, 2022

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Karen M Redden
(74) *Attorney, Agent, or Firm* — Thomas Horstemeyer, LLP

(57) ABSTRACT

A new and distinct cultivar of *Distylium* plant named 'DISmd-09-15', characterized by its compact, upright, and evergreen plant habit, and its ovate-lanceolate shaped leaves, that are dark green once mature and bronze-red in color when young. The inventor believes it could be used as a screening hedge in the South.

3 Drawing Sheets

Botanical designation: *Distylium* sp. hybrid.
Variety denomination: 'DISmd-09-15'.

BACKGROUND OF THE INVENTION

The present invention relates to a new and distinct cultivar of *Distylium* plant, botanically known as *Distylium* sp. hybrid (*Distylium myricoides* x *Distylium racemosum*), a member of the Hamamelidaceae, and hereinafter referred to by the cultivar name 'DISmd-09-15'. This cultivar represents a new *Distylium*, an evergreen shrub grown for landscape use.

The new *Distylium* 'DISmd-09-15' was discovered and selected from a breeding program conducted by the inventor at a horticulture farm in Watkinsville, Ga. 'DISmd-09-15' originated as a seedling that arose from a group of seedlings from the open pollination of the female parent *Distylium* 'PIIDIST-II' Blue Cascade™ (U.S. Plant Pat. No. 24,409) in the fall of 2014. 'DISmd-09-15' was selected as a single unique plant in the summer of 2015 from among the resulting seedlings.

Asexual propagation of the new cultivar by semi-hard stem cuttings has been continued in Watkinsville, Ga. since 2015. Observations of the resulting *Distylium* 'DISmd-09-15' has determined that the unique features of this new cultivar are stable and reproduced true-to-type in successive generations of such asexual propagation.

SUMMARY OF THE INVENTION

Plants of the new *Distylium* cultivar 'DISmd-09-15' have not been observed under all possible environmental conditions. The phenotype may vary somewhat with variations in environment and cultural practices such as light, temperature, soil and rainfall without, however, any variance in genotype.

The following traits have been repeatedly observed and represent the unique and distinguishing characteristics of the cultivar named 'DISmd-09-15'. In combination, these traits set 'DISmd-09-15' apart from all other existing varieties of *Distylium* known to the inventors:

1. 'DISmd-09-15' exhibits a compact, upright, and evergreen growth habit;
2. 'DISmd-09-15' exhibits ovate-lanceolate leaves that are dark green when mature and bronze-red when immature or juvenile; and
3. 'DISmd-09-15' has thus far exhibited cold hardiness to about 20 degrees Fahrenheit.

Plants of 'DISmd-09-15' differ from its female parent plant, Blue Cascade™ by having a more upright, fastigiate canopy or growth habit. 'DISmd-09-15' also differs from Blue Cascade™ in having new growth that is a bronze-red, maturing to dark green, in contrast to the new growth of Blue Cascade™, which is a blue-purple color. Plants of 'DISmd-09-15' (not patented) also differ from related cultivar 'DISmd-24-18' which has new growth that is bronze-pink in color, in contrast to the bronze-red of 'DISmd-09-15'.

The upright growth habit lends this plant to being utilized as a screening plant by landscapers and gardeners alike.

BRIEF DESCRIPTION OF THE DRAWINGS

The accompanying color photographs illustrate the overall appearance and distinct characteristics of the new cultivar 'DISmd-09-15', including foliage characteristics, showing the colors as true as it is reasonably possible. Colors in the photographs may differ slightly from the color values cited in the detailed botanical description, which accurately describes the colors of 'DISmd-09-15'.

The photograph labeled

The photograph labeled

The photograph labeled

DETAILED DESCRIPTION

Figure 1:
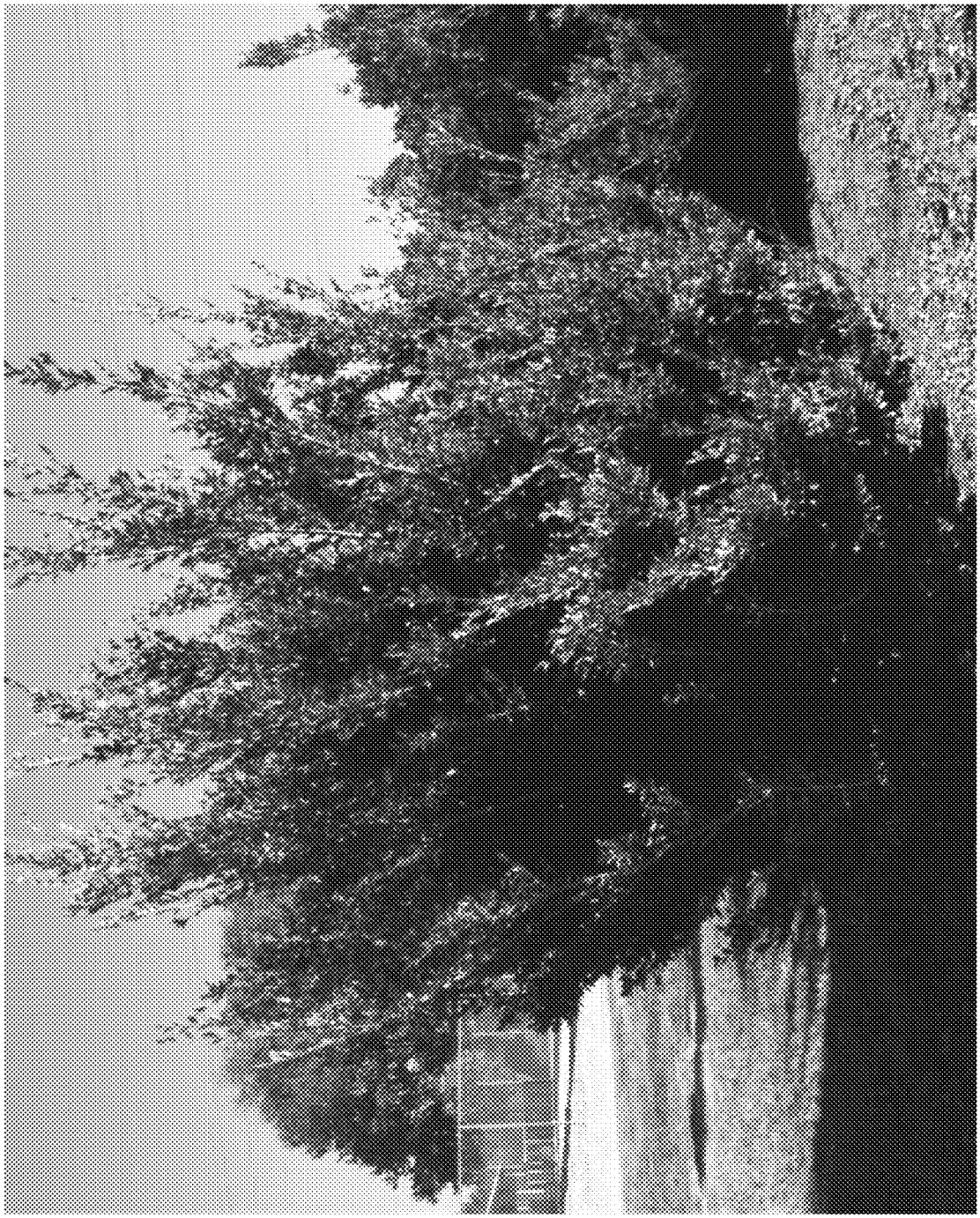
FIG. 1 depicts 'DISmd-09-15' plants with no damage grown at the horticultural farm in Watkinsville, Ga. Plants are 7 years old, and the photo was taken in Spring 2021.
Figure 2:
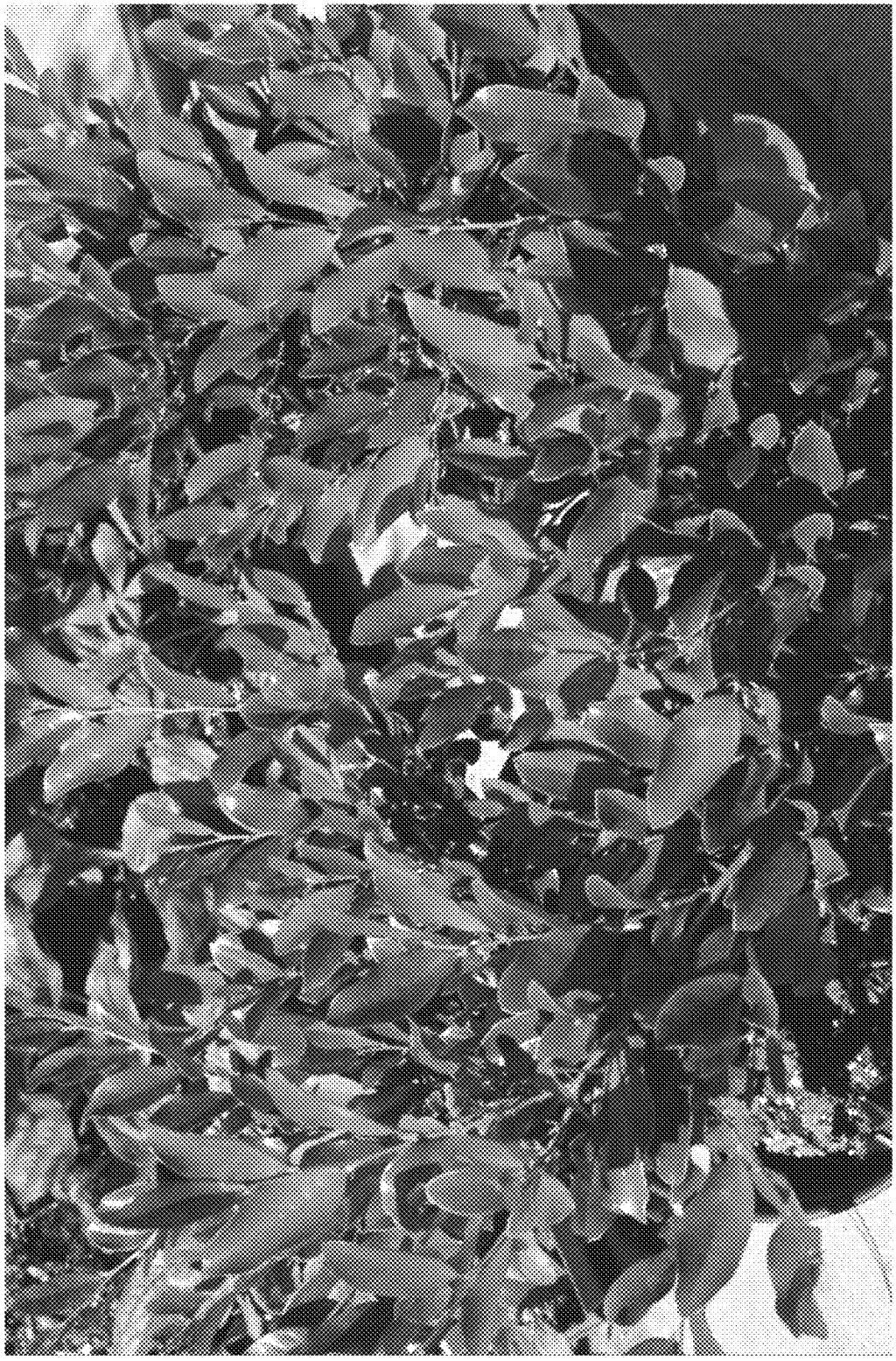
FIG. 2 depicts a close up of the dark green leaves of 'DISmd-09-15' on a 7-year-old plant. The photo was taken in Summer 2021 in Watkinsville, Ga.
Figure 3:
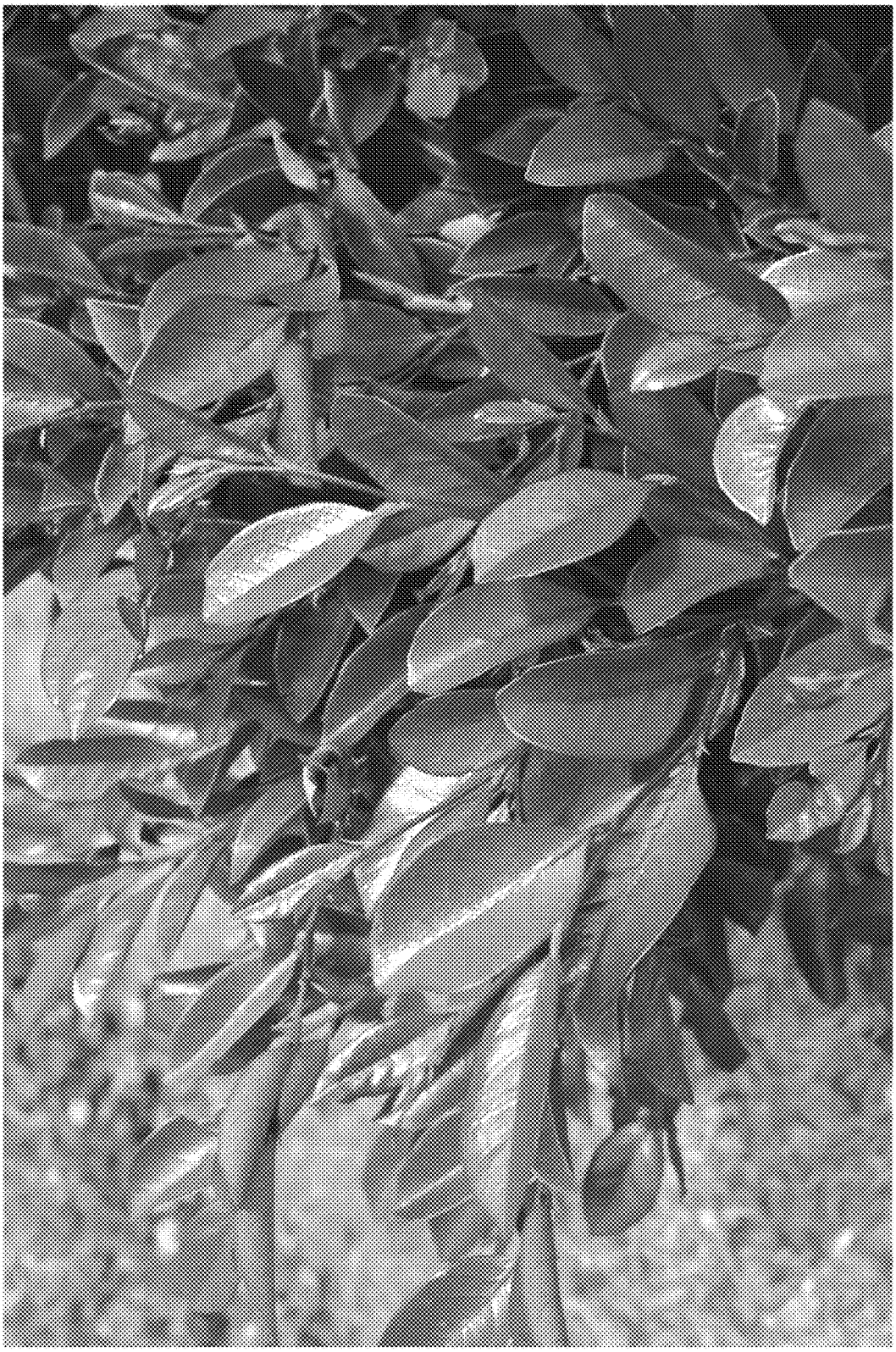
FIG. 3 depicts a close up of the bronze-red new growth leaves of 'DISmd-09-15'. The plant in the photograph is 7 years old, and the photo was taken in Summer 2021 in Watkinsville, Ga.

The following traits have been consistently observed in the original plant of this new variety and in asexually propagated progeny grown from Watkinsville, Ga., and, to the best knowledge of the inventors, their combination forms the unique characteristics of the new variety 'DISmd-09-15'.

Throughout this specification, color names beginning with a small letter signify that the name of that color, as used in common speech, is aptly descriptive. Color names beginning with a capital letter designate values based upon The Royal Horticultural Society Colour Chart, 2015 Edition, except when general terms of ordinary dictionary significance are used.

The aforementioned photographs and following observations, measurements, and values describe plants of the Genus species cultivar named 'DISmd-09-15'. Plants used for the description were approximately two years old and were grown in three-gallon containers under outdoor conditions in Watkinsville, Ga. The average low temperatures during the winter ranged from about 33-42° F., and the average high temperatures during the Summer ranged from about 85-92° F. in summer.

Botanical classification: *Distylium* sp. hybrid, cultivar 'DISmd-09-15'.

Parentage: *Distylium* sp. hybrid. (Female or seed parent: Blue Cascade™ *Distylium*. Male or pollen parent: unknown/open pollenated).

Propagation: Stem cuttings, asexual propagation.

Time to initiate roots in summer: About 3 to 4 weeks at about 32° C.

Time to produce a rooted young plant: About 4 months at about 32° C.

Plant description: Medium form, well branched, diffuse and extensive.

*Usage*.—Landscaping hedge appropriate for commercial use, home garden, and the like.

*Root description*.—Medium, well branched.

*Plant size*.—The original plant, now about 7 years old in the ground, is about 304 cm high from the soil level to the top of the foliage canopy and about 183 cm wide.

*First year stems*.—Having a diameter of about 3 mm. Shape: Round. Fine pubescence. Few small lenticels about 1 mm in diameter and N199B in color.

*Length*.—About 22 cm and very flexible.

*First year stem color*.—187B.

*Second year and older stems*.—Have a diameter of about 5 mm or more. Shape: Round. Length: about 92 cm and stems easily broken once mature. Smooth, no pubescence.

*Second year and older stem color*.—187B.

*Stem strength*.—Flexible when young, less flexible when mature.

*Internode length*.—About 1.5 cm.

*Trunk diameter*.—About 12 cm at soil level.

*Trunk color*.—199B.

*Bark*.—Does not exfoliate, covered with many lenticels about 1 mm in diameter and N199B in color.

Vegetative bud description:

*Arrangement*.—Alternate.

*Shape*.—Ovate with fused, pubescent bud scales.

*Size*.—About 1 mm in length and about 0.5 mm in width.

*Color*.—200A.

Foliage description:

*Arrangement*.—Alternate, simple.

*Length*.—About 4 cm.

*Width*.—About 12 mm.

*Shape*.—Ovate-lanceolate.

*Apex*.—Acute.

*Base*.—Cuneate.

*Margin*.—Entire, occasionally undulating.

*Texture* (*upper and lower surfaces*).—Smooth and thick, leathery.

*Venation pattern*.—Pinnate.

*Venation color* (*upper and lower surfaces*).—Midrib color is 187A and secondary vein color is 187A.

*Color of emerging foliage* (*upper surface*).—173A.

*Color of emerging foliage* (*lower surface*).—140B.

*Color of mature foliage* (*upper surface*).—N134B.

*Color of mature foliage* (*lower surface*).—140B.

*Petiole length*.—About 6 mm.

*Petiole diameter*.—About 1 mm.

*Petiole shape*.—Elliptical.

*Pubescence*.—Fine, 199A in color.

*Petiole color* (*upper and lower surfaces*).—140C.

Flower description: Detailed botanical data for the flowers of the new *Distylium* are not readily available, and are not considered a distinguishing characteristic of the new cultivar. The original plant has flowered only once in 7 years in ground, but data could not be obtained due to short duration of bloom. *Distylium* typically flower in January and are more often than not affected by late frost or cold snaps.

Fruit description: As described above for flower data, detailed botanical data for fruit is also not readily available for the new *Distylium* 'DISmd-09-15'.

Disease/pest resistance: Plants of the new *Distylium* grown in the nursery and garden have not been noted to be susceptible to pathogens, pests, or disease.

Weather and temperature tolerance: 'DISmd-09-15' is cold hardy in USDA Cold Hardiness Zones 7-9.

It is claimed:

1. A new and distinct cultivar of *Distylium* named 'DISmd-09-15' as illustrated and described herein.

* * * * *